United States Patent [19]

Sharp

[11] Patent Number: 4,992,046

[45] Date of Patent: Feb. 12, 1991

[54] DENTAL MOUTH PROP FOR ISOLATING A TOOTH

[75] Inventor: Harry K. Sharp, Memphis, Tenn.

[73] Assignee: The University of Tennessee Research Corporation, Knoxville, Tenn.

[21] Appl. No.: 305,809

[22] Filed: Feb. 3, 1989

[51] Int. Cl.⁵ .............................................. A61C 17/06
[52] U.S. Cl. ...................................... 433/93; 433/91; 433/140
[58] Field of Search ............................ 433/91, 93, 140

[56] References Cited

U.S. PATENT DOCUMENTS

| | | | |
|---|---|---|---|
| 1,229,595 | 6/1917 | DuBrul | 433/140 X |
| 1,986,275 | 1/1935 | Lowry | 32/33 |
| 2,103,115 | 12/1937 | Mizzy et al. | 433/140 |
| 2,706,334 | 4/1955 | Daigle | 32/33 |
| 2,823,455 | 2/1958 | Sprague | 433/93 |
| 2,885,783 | 5/1959 | Golden | 433/93 X |
| 2,937,445 | 5/1960 | Erickson | 32/33 |
| 3,027,643 | 4/1962 | Cohen | 32/33 |
| 3,396,468 | 8/1968 | Dayhoff | 433/93 |
| 4,053,984 | 10/1977 | Moss | 433/140 X |
| 4,215,984 | 8/1980 | Reichley | 433/93 |
| 4,259,067 | 3/1981 | Nelson | 433/93 |
| 4,260,378 | 4/1981 | O'Neil | 433/93 |

FOREIGN PATENT DOCUMENTS 505545 9/1954 Canada .............................. 433/140

Primary Examiner—Robert P. Swiatek
Assistant Examiner—Nicholas A. Lucchesi

[57] ABSTRACT

A dental mouth prop for maintaining the jaws of a dental patient in an opened condition includes a body for isolating a posterior tooth to be worked upon and for facilitating the evacuation of saliva and other fluids from the region of the mouth around the isolated tooth. The body includes a sidewalls positionable on opposite sides of the tooth to be worked upon and which are joined together so as to form a workspace-defining cavity between the sidewalls. The body also includes hollow portions positionable adjacent the gum tissue of the mandibular arch for collecting and extracting fluids which migrate to the region adjacent the isolated tooth. The prop also includes a bite flap member engageable by the teeth of the mandibular or maxillary arch opposite the tooth to be worked upon and which is pivotally attached to the prop body to accommodate pivotal movement of the flap member to a position corresponding to the occlusal bite plane of the engaging teeth.

16 Claims, 1 Drawing Sheet

DENTAL MOUTH PROP FOR ISOLATING A TOOTH

BACKGROUND OF THE INVENTION.

This invention relates generally to dental appliances and relates more particularly to a mouth prop positionable within the mouth of a dental patient.

While performing various dental procedures on a preselected tooth within the mouth of a patient, it is highly desirable that the tooth be as dry as possible. This is especially true in teeth restoration processes involving the application of sealants to pits and fissures. Such a process, for example, may require that the occlusal surface of a tooth be washed and dried and subsequently maintained in a dry condition prior to the application of the sealant. It has been found that the task of maintaining the tooth in a dry condition is facilitated by isolating the tooth from surrounding mouth tissue which may otherwise wet the tooth.

Conventional techniques for isolating a tooth commonly involve the wedging of cotton rolls between the tooth and surrounding tissue for absorbing fluids which may move into the region surrounding the tooth. However, cotton rolls must be typically replaced during the course of a dental operation, and the process involved in replacing cotton rolls is commonly cumbersome and time-consuming. In addition, it is very easy to contaminate the tooth with fluids each time that the rolls are changed.

Other techniques of isolating a tooth involve the use of a rubber dam and a clamp. However, the clamp is normally uncomfortable and usually requires an injection of a local anesthetic. Alternative techniques for isolating a tooth involve devices which either have no capacity for fluid evacuation, cannot adapt to variations in relationship between the maxillary and mandibular arches, are complicated in construction, are difficult to use, provide inadequate isolation or are relatively expensive.

Accordingly, it is an object of the present invention to provide a new and improved dental appliance for isolating a preselected tooth of a dental patient for working upon the tooth.

Another object of the present invention is to provide such an appliance which facilitates the maintenance of a dry working field about the isolated tooth.

Still another object of the present invention is to provide such an appliance which performs the dual functions of isolating a preselected tooth of the patient and maintaining the jaws of the patient in an opened condition while the tooth is being worked upon.

Yet another object of the present invention is to provide such an appliance which is relatively comfortable when positioned within the mouth of a patient.

A further object of the present invention is to provide such an appliance which adapts to variations in occlusal relationships of the maxillary and mandibular arches.

A still further object of the present invention is to provide such an appliance which is uncomplicated to use and relatively inexpensive to construct.

A yet further object of the present invention is to provide such an appliance which can be easily sterilized for reuse.

SUMMARY OF THE INVENTION.

This invention resides in a mouth prop for use while working upon a preselected tooth of a dental patient.

The mouth prop includes a body for isolating a preselected tooth of a dental patient including a pair of sidewalls positionable on opposite sides of a preselected tooth so as to maintain a separation between the tooth and the mouth tissue positioned adjacent and on opposite sides of the tooth. The body also includes means for joining the sidewalls together so that a tooth-accepting slot and a workspace-defining cavity is provided between the sidewalls. The cavity has an opening providing access to the cavity interior, and the tooth-accepting slot communicates with the cavity. When the mouth prop is operatively positioned within the mouth, the preselected tooth projects through the tooth-accepting slot and into the cavity interior.

DETAILED DESCRIPTION OF THE ILLUSTRATED EMBODIMENTS.

Figure 1:
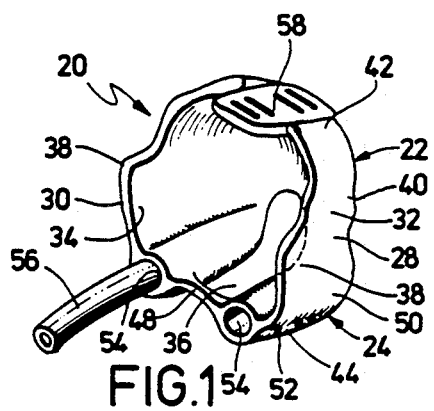
FIG. 1 is a perspective view of one embodiment of a dental mouth prop adapted for use while working on posterior teeth in the mandibular arch of a patient's mouth.

Turning now to the drawings in greater detail and considering first FIG. 1, there is illustrated an embodiment of a dental appliance or mouth prop, generally indicated 20, for propping the mouth of a dental patient in an opened condition and for isolating preselected ones of the posterior teeth located in the patient's mandibular arch. In this connection and with reference to FIGS. 1 and 5, the prop 20 includes means 22 for maintaining the mandibular and maxillary arches of the patient apart and for maintaining a separation between the teeth T (FIG. 5) to be worked upon and the tissue of the mouth normally positioned adjacent the cheek side of the teeth and the tongue side of the teeth. The prop 20 also includes means 24 for facilitating the removal of saliva, water and other fluids from within the mouth which may normally accumulate adjacent the teeth T during the performance of a dental procedure.

Figure 2:
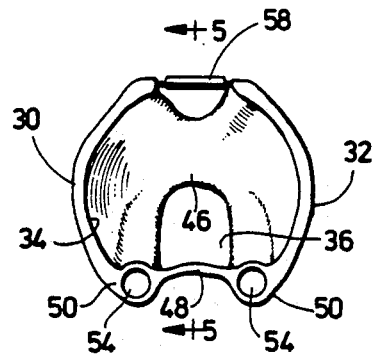
FIG. 2 is a front elevational view of the FIG. 1 mouth prop as seen generally from the left in FIG. 1.

The maintaining means 22 includes a body 28 including a pair of sidewalls 30, 32 joined together in a manner described herein so as to define a forwardly-opening cavity 34 between opposing portions of the sidewalls 30, 32 and a teeth-accepting slot 36. As best shown in FIGS. 1-4, the sidewalls 30, 32 define relatively smooth inside and outside surfaces which are rounded in shape so as to provide the surfaces of the body 28 with somewhat of an eggshell-like curvature or ovoid form. As best shown in FIG. 2, the rounded inside surfaces of the body 28 provide the cavity 34 with a relatively broad, expansive working area, and the rounded outside surfaces of the body 28 enhance the comfort of the prop 20 when the prop 20 is operatively positioned within the patient's mouth. The body 28 is preferably constructed of a relatively hard, nonporous plastic or another suitably rigid material which is impervious to fluids and which is capable of being sterilized between uses without damage to the body 28.

Figure 5:
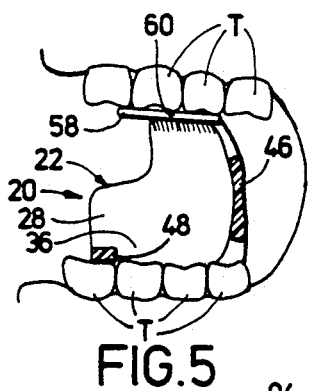
FIG. 5 is a cross-sectional view of the FIG. 1 mouth prop shown operatively positioned within the mouth of a dental patient and wherein the cross-sectional view is taken about on line 5—5 of FIG. 2.

The cavity 34 defined between the sidewalls 30, 32 opens generally forwardly when the prop 20 is positioned within the mouth to provide access to the cavity interior for working upon the teeth T (FIG. 5). Accordingly, each sidewall 30 or 32 includes a forward portion 38 and an opposite, rearward portion 40 positionable at the rear of the mouth. In addition, the body 22 is positionable within the mouth in a prescribed orientation so that the sidewalls 30, 32 are positioned on opposite sides of the teeth T and so that the teeth T project upwardly through the slot 36 and into the cavity 34. Accordingly, each sidewall 30 or 32 includes an upper portion 42 and a lower portion 44.

With reference to FIGS. 1, 2 and 5, the sidewalls 30, 32 are joined to one another by a first section 46 which connects the rearward portions 40, 40 of the sidewalls 30, 32 together. The first section 46 defines a relatively smooth outer surface for spanning the patient's mouth tissue joining the mandibular and maxillary arches. The sidewalls 30, 32 are also joined together by a second section 48 which connects the forward portions 38, 38 of the sidewalls 30, 32 together and which is adapted to extend transversely across the ones of the patient's teeth positioned immediately forwardly of the preselected teeth T. Defined between the first and second sections 46, 48 is the teeth-accepting slot 36 which is appropriately sized to accept the teeth T.

The body 28 also includes means facilitating the evacuation of saliva or other fluids which tend to accumulate in the mouth while the teeth T are being worked upon. In this connection, the body 28 includes a hollow portion 50 associated with each sidewall 30 or 32 and within which a plurality of openings 52 are defined through the sides of the hollow portion 50. The hollow portions 50, 50 are shaped so that when the prop 20 is used, the hollow portions 50, 50 are comfortably positioned against the gum tissue located on opposite sides of the teeth T, and the openings 52 permit fluids to pass from outside the hollow portion 50 to the inside thereof. The hollow portion 50 further includes a forwardly-opening exit passageway 54 accommodating the removal of fluids from the interior of the hollow portion 50. In this connection, the exit passageway 54 is shaped to snugly receive the suction tube of a saliva ejector 56 (only one shown in FIG. 1) with which fluids which accumulate in the hollow portions 50 can be withdrawn. Therefore, fluids can be continuously evacuated with a saliva ejector from the hollow portions 50, 50 for maintaining a relatively dry working region about the teeth T.

Figure 3:
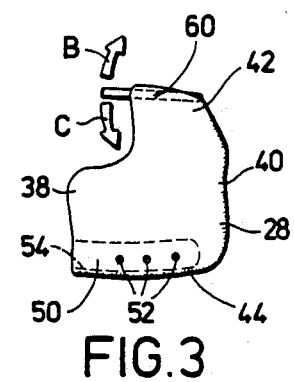
FIG. 3 is a side elevational view of the FIG. 1 mouth prop as seen from the right in FIG. 2.
Figure 4:
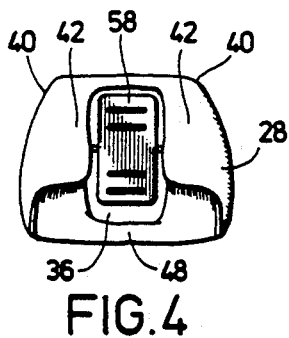
FIG. 4 is a top plan view of the FIG. 1 mouth prop as seen from above in FIG. 2.

The prop 20 further includes means enabling the body 28 to be seated in place within the patient's mouth by biting forces placed upon the prop 20 by the patient. In this connection, the prop 20 includes an elongate platen-like bite flap member 58 connected between the upper portions 42, 42 of the sidewalls 30, 32 for pivotal movement about an axis 60 (FIG. 3) oriented transversely of the body 28. As best shown in FIG. 3, the pivot axis 60 extends through the flap member 58 at a location positioned substantially midway between the ends of the member 58 to accommodate pivotal movement of the ends in the direction of the arrows B and C about the axis 60. When the prop 20 is operatively positioned within the mouth and the patient's jaws are urged toward a closed condition, the teeth in the maxillary arch engage the upper surface of the flap member 58 so that the flap member 58 pivots to a position corresponding with the bite plane of the engaging teeth. Pivoted to correspond with the bite plane, the flap member 58 transmits occlusal forces to the prop body 28 along a path oriented generally parallel to the longitudinal axis of one of the isolated teeth T. Such a transmittal of forces effectively seats the prop 20 within the mouth so that the prop body 28 is prevented from shifting relative to the teeth T while they are being worked upon. The bite flap member 58 provides a further advantage in that its capacity to pivot to a condition corresponding with the bite plane of the upper teeth permits the body 28 to be effectively seated irregardless of possible variations in relationship of the maxillary and mandibular arches when moving the prop 20 from one position to another for isolating different ones of the teeth or when, after suitable cleaning, the prop 20 is used in the mouth of a different patient.

Figure 6:
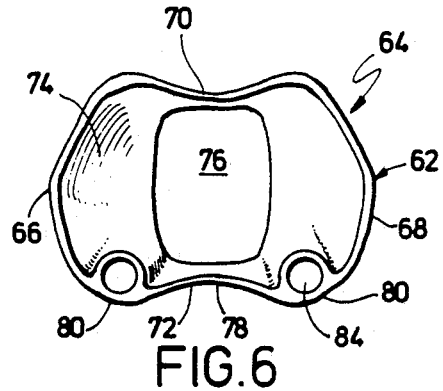
FIG. 6 is a front elevational view of another embodiment of a dental mouth prop adapted for use while working on posterior teeth in the maxillary arch of a patient's mouth.
Figure 7:
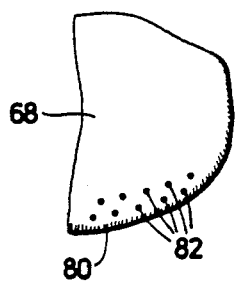
FIG. 7 is a side elevational view of the FIG. 6 mouth prop as seen from the right in FIG. 6.

With reference to FIGS. 6 and 7, there is illustrated an alternative embodiment of a mouth prop, generally indicated 64, which is well-suited for isolating posterior teeth located in the maxillary arch of a dental patient. The prop 64 has a body 62 including two rounded sidewalls 66, 68 joined together by first and second sections 70, 72 for maintaining the sidewalls 66, 68 in spaced relationship so as to define a cavity 74 between opposing portions of the sidewall and a teeth-accepting slot 76. One of the joining sections 72 defines a teeth-receiving groove 78 for accepting the teeth of the mandibular arch located generally opposite the teeth of the maxillary arch to be worked upon.

When the prop 64 is operatively positioned within the mouth of a patient, the sidewalls 66, 68 are positioned on opposite sides of the teeth to be worked upon so that when the jaws are closed upon the prop 64, the teeth to be worked upon protrude through the slot 76 and into the cavity 74. By urging the mandibular and maxillary arches toward a closed condition, the teeth of the arches engage and bear against the first and second sections 70, 72 to hold the prop 64 in place. In this connection, the upper surface of the first section 70 is engageable by the teeth of the maxillary arch positioned forwardly of the teeth to be worked upon, and the surfaces of the groove 78 of the second section 72 are engageable by the teeth in the mandibular arch.

For purposes of extracting saliva and other fluids from the region adjacent the maxillary teeth to be worked upon, the body 62 includes a hollow portion 80 associated with each sidewall 66 or 68 for positioning between the gum tissue of the mandibular arch and the adjacent tissue of the cheek and tongue. Each hollow portion 80 defines a plurality of openings 82 permitting fluid to pass to the interior of the hollow portion 80 and an exit passageway 84 adapted to receive the tube of a saliva ejector (not shown) for extracting fluid which accumulates within the hollow portions 80, 80 of the body 62.

Figure 8:
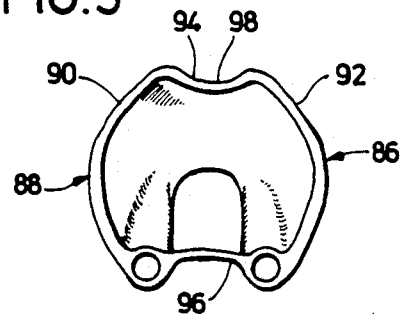
FIG. 8 is a front elevational view of still another embodiment of a dental mouth prop adapted for use while working on posterior teeth in the mandibular arch of a patient's mouth.

It will be understood that numerous modifications and substitutions can be had to the aforedescribed embodiments without departing from the spirit of the invention. For example, although the embodiment 20 of FIGS. 1-5 for isolating teeth of the mandibular arch has been shown and described as including a bite flap member 58 for engaging teeth of the maxillary arch, a prop for isolating teeth of the mandibular arch may not include such a bite flap member. For example, there is illustrated in FIG. 8 an embodiment of a prop, generally indicated 86, having a body 88 including rounded sidewalls 90, 92 joined together by first and second sections 94, 96, respectively, adapted to be engaged by the teeth of the mandibular and maxillary arches when positioned within the mouth. In this connection, the first section 94 defines a teeth-receiving groove 98 for accepting the teeth of the maxillary arch so that when the patient's teeth bear against the first and second sections 94, 96, the prop 86 is securely held in place between the patient's jaws.

Figure 9:
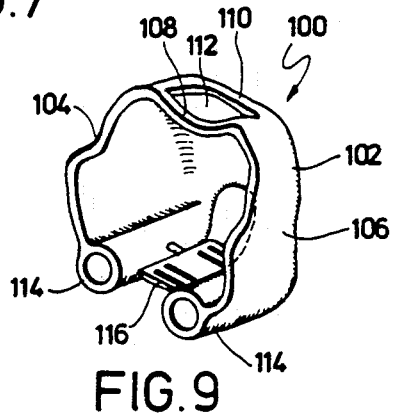
FIG. 9 is a perspective view of yet another embodiment of a dental mouth prop adapted for use while working on posterior teeth in the maxillary arch of a patient's mouth.
Figure 10:
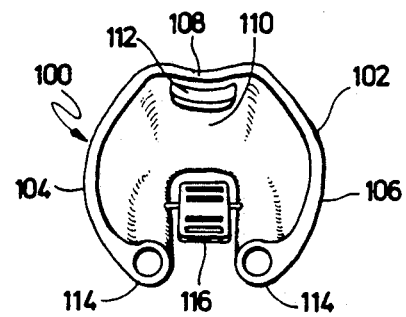
FIG. 10 is a front elevational view of the FIG. 9 mouth prop as seen generally from the left in FIG. 9.

Furthermore, although the embodiment 64 of FIGS. 6 and 7 for isolating teeth of the maxillary arch has been shown and described as not including a bite flap member, a prop for isolating teeth of the maxillary arch may include such a bite flap member. For example, there is illustrated in FIGS. 9 and 10 an embodiment of a flap member-including prop, generally indicated 100, having a body 102 including rounded sidewalls 104, 106 joined together by first and second sections 108, 110, respectively. A slot 112 is provided between the sections 108, 110 and is adapted to accept the teeth of the maxillary arch to be worked upon. The first section 108 is gently arched so that the slot 112 accommodates the palate. A hollow portion 114 is attached to each sidewall 104 or 106 adjacent the bottom thereof for facilitating the collection and removal of fluids from the region of the mouth to be worked upon, and a bite flap member 116 is supported between the hollow portions 114, 114 for pivotal movement relative thereto. When the prop 100 is operatively positioned within the mouth, teeth in the maxillary arch bear against the first section 108 and teeth in the mandibular arch bear against the bite flap member 116. It will be understood that the advantages attending the bite flap member 58 of the embodiment 20 of FIGS. 1-5, such as the transmission of occlusal forces and capacity to pivot to a plane corresponding to the occlusal bite plane of the engaging teeth, apply to the bite flap member 116 as well.

Accordingly, the aforedescribed embodiments are intended for the purpose of illustration and not as limitation.

What is claimed is:

1. A mouth prop for use while working upon a preselected tooth of a dental patient, said prop comprising:
    a body for isolating a preselected tooth of a patient including a pair of sidewalls of relatively rigid construction and positionable on opposite sides of the preselected tooth so as to maintain a separation between the tooth and the mouth tissue positioned adjacent and on opposite sides of the tooth and means for joining the sidewalls together so that a tooth-accepting slot and a workspace-defining cavity is provided between the sidewalls, said cavity having an opening providing access to the cavity interior for working upon the preselected tooth and said tooth-accepting slot communicating with said cavity so that when the prop is operatively positioned within the mouth, the preselected tooth projects through the tooth-accepting slot and into the cavity interior and the interior of the workspace-defining cavity is isolated from the mouth tissue positioned adjacent and on opposite sides of the tooth by the body sidewalls so that fluids are prevented from entering the cavity interior through the body sidewalls;
    said body further including means defining a hollow portion associated with each of the two sidewalls and positioned generally beneath the workspace-defining cavity for extending generally along the gum tissue of the mandibular arch so that when the prop is operatively positioned within the mouth, the two hollow portions are positioned on opposite sides of the posterior teeth of the mandibular arch, each hollow portion defining at least one opening permitting fluids to enter the inside of the hollow portion from the mouth region adjacent the gum tissue and each hollow portion further defining an exit passageway accommodating the removal of fluids from the inside of the hollow portion, the inside of the hollow portion being separated from the cavity interior so that no communication is provided therebetween so that fluids which enter the hollow portion cannot enter the cavity interior; and
    each sidewall including an upper portion for bounding the workspace-defining cavity and a lower portion incorporating said means defining said hollow portion, each of said upper and lower portions being shaped so that its outer surface is rounded and substantially convex in form and the upper and lower portions are joined to one another in a region which is smooth, continuous and devoid of sharp corners as a path is traced between the upper and lower sidewall portions so that the sidewalls collectively provide the body with a substantially ovoid form and so that when operatively positioned within the patient's mouth, the mouth prop fits comfortably therein.

2. The mouth prop of claim 1 wherein the material out of which the body is constructed is impervious to fluids.

3. The mouth prop of claim 1 wherein the preselected tooth of a patient is a posterior tooth of one of the maxillary and mandibular dental arches and each sidewall includes a back portion positionable at the rear of the mouth when the prop is operatively positioned therein and the means for joining includes a section formed with so as to join the back portions of the sidewalls for spanning the tissue located at the rear of the mouth which extends between the maxillary and mandibular arches of the patient.

4. The mouth prop of claim 3 wherein said section is a first section and the means for joining includes a second section formed with so as to join the sidewalls forwardly of the first section so that the tooth-accepting slot is defined between said first and second sections.

5. The mouth prop of claim 1 wherein said exit passageway is adapted to be connected to a saliva ejector for the removal of fluids from the hollow portion.

6. The mouth prop of claim 1 further including a bite flap member positioned between the sidewalls for engagement by teeth in one of the maxillary and mandibular arches generally opposite the isolated tooth, said bite flap member being connected to the sidewalls for pivotal movement relative thereto so that when the jaws are urged toward a closed condition about the prop so that the teeth of said one arch bear against the bite flap member, the bite flap member is permitted to pivot to a position corresponding with the occlusal bite plane of the teeth of said one arch.

7. The mouth prop of claim 6 wherein said bite flap member is connected between said sidewalls for pivotal movement relative thereto about a pivot axis oriented transverse of the teeth in said one arch.

8. The mouth prop of claim 7 wherein said bite flap member is elongated in shape so as to define two opposite ends and said axis of pivot is oriented generally perpendicular to the longitudinal axis of said bite flap member and is located substantially midway between the ends of the bite flap member.

9. An appliance for maintaining the jaws of a dental patient in an opened condition for working upon a preselected tooth in the mouth of the patient, said appliance comprising:

a body for isolating a preselected tooth of a patient including a pair of sidewalls of relatively rigid construction and positionable on opposite sides of the preselected tooth so as to maintain a separation between the tooth and the mouth tissue positioned adjacent and on opposite sides of the tooth and for supporting the jaws of the patient in an opened condition, said body further including means for joining the sidewalls together so that a tooth-accepting slot and a cavity is defined between the sidewalls and said sidewall joining means being engaged by the teeth in the maxillary and mandibular arches when the appliance is positioned within the mouth, said cavity having an opening providing access to the cavity interior for working upon the preselected tooth and said tooth-accepting slot communicating with said cavity so that when the appliance is operatively positioned within the mouth and the teeth of the maxillary and mandibular arches bear against the sidewall-joining means, the preselected tooth projects through the tooth-accepting slot and into the cavity interior and the interior of the cavity is isolated from the mouth tissue positioned adjacent and on opposite sides of the preselected tooth by the body sidewalls so that fluids are prevented from entering the cavity interior through the body sidewalls;

said body further including means defining a hollow portion associated with each of the two sidewalls and positioned generally beneath the workspace-defining cavity for extending generally along the gum tissue of the mandibular arch so that when the appliance is operatively positioned within the mouth, the two hollow portions are positioned on opposite sides of the posterior teeth of the mandibular arch, each hollow portion defining at least one opening permitting fluids to enter the inside of the hollow portion from the mouth region adjacent the gum tissue and each hollow portion further defining an exit passageway accommodating the removal of fluids from the inside of the hollow portion, the inside of the hollow portion being separated from the cavity interior so that no communication is provided therebetween so that fluids which enter the hollow portion cannot enter the cavity interior; and each sidewall including an upper portion for bounding the workspace-defining cavity and a lower portion incorporating said means defining said hollow portion, each of said upper and lower portions being shaped so that its outer surface is rounded and substantially convex in form and the upper and lower portions are joined to one another in a region which is smooth, continuous and devoid of sharp corners as a path is traced between the upper and lower sidewall portions so that the sidewalls collectively provide the body with a substantially ovoid form and so that when operatively positioned within the patient's mouth, the appliance fits comfortably therein.

10. The appliance of claim 9 wherein the upper portion of each sidewall has an inner surface which is substantially concave in shape.

11. The appliance of claim 9 wherein the preselected tooth of a patient includes a posterior tooth of one of the maxillary and mandibular dental arches and each sidewall includes a back portion positionable at the rear of the mouth when the appliance is operatively positioned therein and the sidewall-joining means includes a first section joining the back portions of the sidewalls for spanning the tissue located at the rear of the mouth, which tissue extends between the maxillary and mandibular arches of the patient, and said sidewall-joining means includes a second section joining the sidewalls forwardly of said first section so that said tooth-accepting slot is defined between said first and second sections.

12. The appliance of claim 9 wherein each hollow portion defines a plurality of openings permitting fluids to enter the inside of the hollow portion from the mouth region adjacent the gum tissue.

13. The appliance of claim 12 wherein said openings are defined along the length of each hollow portion.

14. The appliance of claim 9 wherein the preselected tooth is a posterior tooth in one of the maxillary and mandibular arches and the appliance further includes a bite flap member positioned between the sidewalls for engagement by teeth positioned generally opposite said posterior tooth, said bite flap member being connected between the sidewalls for pivotal movement relative thereto so that when the jaws are urged toward a closed condition about the appliance so that the opposite teeth bear against the bite flap member, the bite flap member is permitted to pivot to a position corresponding with the occlusal bite plane of the opposite teeth.

15. The appliance of claim 14 wherein the bite flap member is permitted to pivot in such a manner relative to the sidewalls so that when the opposite teeth operatively bear against the bite flap member, the bite flap member transfers occlusal forces to the body in a direction substantially parallel to the longitudinal axis of the preselected tooth for seating the body in place.

16. A dental mouth prop for isolating a tooth within the mouth of a dental patient and for maintaining the patient's jaws in an opened condition for working upon the isolated tooth, said prop comprising:

a body including a pair of sidewalls of relatively rigid construction and positionable on opposite sides of the isolated tooth and means for joining the sidewalls together so that a teeth-accepting slot and workspace-defining cavity is provided between the sidewalls, the sidewall-joining means adapted to be engaged by the teeth in the maxillary and mandibular arches of a patient and said sidewalls being positionable on opposite sides of the isolated tooth for maintaining a separation between the isolated tooth and the cheek and tongue tissue positioned on opposite sides of the isolated tooth, said cavity having an opening providing access to the cavity interior for working upon the isolated tooth and said teeth-accepting slot communicating with said cavity so that when the prop is operatively positioned within the mouth so that the teeth of the maxillary and mandibular arches bear against the sidewall-joining means, the preselected tooth projects through the teeth-accepting slot and into the cavity interior and so that the interior of the cavity is isolated from the cheek and tongue tissue positioned on opposite sides of the isolated tooth by the body sidewalls so that fluids are prevented from entering the cavity interior through the body sidewalls, said sidewalls and sidewall-joining means providing a relatively expansive cavity between the body sidewalls for working upon the isolated tooth; and said body further including means defining a hollow portion associated with each of the two sidewalls and positioned generally beneath the workspace-defining cavity for extending generally along the gum tissue of the mandibular arch so that when the prop is operatively positioned within the mouth, the two hollow portions are positioned on opposite sides of the posterior teeth of the mandibular arch, each hollow portion defining at least one opening permitting fluids to enter the inside of the hollow portion from the mouth region adjacent the gum tissue and each hollow portion further defining an exit passageway accommodating the removal of fluids from the inside of the hollow portion, the inside of the hollow portion being separated from the cavity interior so that no communication is provided therebetween so that fluids which enter the hollow portion cannot enter the cavity interior; and each sidewall including an upper portion for bounding the workspace-defining cavity and a lower portion incorporating said means defining said hollow portion said upper and lower portions being shaped so that its outer surface is rounded and substantially convex in form and the upper and lower portions are joined to one another in a region which is smooth, continuous and devoid of sharp corners as a path is traced between the upper and lower sidewall portions so that the sidewalls, with the sidewall-joining means, collectively provide the body with a substantially ovoid form to enhance the comfort of the prop when positioned within the patient's mouth.

* * * * *

UNITED STATES PATENT AND TRADEMARK OFFICE
CERTIFICATE OF CORRECTION

PATENT NO.   :   4,992,046

DATED        :   February 12, 1991

INVENTOR(S)  :   R. Wiley Carr and Harry K. Sharp

It is certified that error appears in the above-identified patent and that said Letters Patent is hereby corrected as shown below:

On the title page, under item [19], "Sharp" should be --Carr--; and item [75] should read as follows:

--[75]   R. Wiley Carr, Chattanooga and
Harry K. Sharp, Memphis, both of Tenn.--.

Signed and Sealed this

Twenty-eighth Day of July, 1992

*Attest:*

DOUGLAS B. COMER

*Attesting Officer*   *Acting Commissioner of Patents and Trademarks*